United States Patent
Lee et al.

(10) Patent No.: US 7,248,909 B2
(45) Date of Patent: Jul. 24, 2007

(54) METHOD AND APPARATUS FOR DYNAMICALLY MONITORING MULTIPLE IN VIVO TISSUE CHROMOPHORES

(75) Inventors: Jangwoen Lee, Irvine, CA (US); Bruce J. Tromberg, Irvine, CA (US); Albert E. Cerussi, Lake Forrest, CA (US); Matthew Brenner, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 168 days.

(21) Appl. No.: 11/103,963

(22) Filed: Apr. 12, 2005

(65) Prior Publication Data

US 2005/0228246 A1   Oct. 13, 2005

Related U.S. Application Data

(60) Provisional application No. 60/561,839, filed on Apr. 13, 2004.

(51) Int. Cl.
*A61B 5/00* (2006.01)
(52) U.S. Cl. .................. 600/322; 600/326; 600/328
(58) Field of Classification Search ............... 600/322, 600/323, 328, 326
See application file for complete search history.

(56) References Cited

U.S. PATENT DOCUMENTS

| | | | |
|---|---|---|---|
| 4,510,938 A * | 4/1985 | Jobsis et al. | 600/344 |
| 6,611,320 B1 * | 8/2003 | Lindberg et al. | 356/40 |
| 6,622,095 B2 * | 9/2003 | Kobayashi et al. | 600/322 |
| 2003/0023172 A1 | 1/2003 | Tromberg et al. | |
| 2003/0184757 A1 | 10/2003 | Bevilacqua et al. | |

OTHER PUBLICATIONS

Cuccia et al., In Vivo Quant. of Opt. Cont. Agent Dyn. in Rat Tumors By Use of DOS with MRI Coregistration, Applied Optics, vol. 42, No. 16, Jun. 2003.

Merritt et al., Coregistration of DOS and MRI in a Rat Tumor Model, Applied Optics, vol. 42, No. 16, Jun. 2003.

* cited by examiner

*Primary Examiner*—Eric Winakur
*Assistant Examiner*—Etsub Berhanu
(74) *Attorney, Agent, or Firm*—Vista IP Law Group LLP (57) ABSTRACT

A device and method utilizes a broadband diffuse optical spectroscopy (DOS) system to dynamically calculate the concentrations of multiple chromophores in vivo using a non-invasive probe. The device and method permit dynamic monitoring of multiple in vivo tissue chromophores non-invasively with sensitivities necessary for effective therapeutic monitoring. The device includes a probe containing first and second source optical fibers as well as first and second detector optical fibers. The probe is placed adjacent to a sample of interest and detects reflected light which is passed to a proximally located detector and spectrometer. The concentrations of multiple chromophores are determined in real time. In a preferred embodiment, the multiple tissue chromophores include at least two of methemoglobin (MetHb), deoxyhemoglobin (Hb-R), oxyhemoglobin (Hb-$O_2$), water ($H_2O$), and methylene blue (MB). The device and method can be used quantify and monitor methemoglobin formation in subjects suffering from methemoglobinemia.

17 Claims, 9 Drawing Sheets

METHOD AND APPARATUS FOR DYNAMICALLY MONITORING MULTIPLE IN VIVO TISSUE CHROMOPHORES

REFERENCE TO RELATED APPLICATIONS

This Application claims priority to U.S. Provisional Patent Application No. 60/561,839 filed on Apr. 13, 2004. The '839 Application is incorporated by reference as if set forth fully herein.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Grant No. 445574-30133 awarded by the National Institutes of Health (Laser Microbeam and Medical Program: LAMMP) and Department of Defense (Air Force) Contract No. AF49620-00-10371.

FIELD OF THE INVENTION

The field of the invention generally relates to methods and devices used in diffuse optical spectroscopy. More specifically, the field of the invention generally relates to broadband diffuse optical spectroscopy methods and devices which are able to dynamically monitor multiple in vivo tissue chromophores.

BACKGROUND OF THE INVENTION

In vivo quantitative non-invasive dynamic monitoring of biochemical processes is one of the most difficult and important challenges in medical diagnostics. New near infrared (NIR) spectroscopy has been widely employed for this purpose. However, conventional methods generally do not separate light absorption from scattering, and as a result, do not report absolute biochemical concentrations in tissue. Advances in time and frequency domain NIR measurements have resulted in the development of quantitative approaches. However, these methods typically rely on a limited number of optical wavelengths and therefore have poor sensitivity to multiple analytes over a broad range of concentrations.

Traditional diagnostic methods for methemoglobinemia patients include pulse oximetry, arterial blood gas analysis, and co-oximetry. Pulse oximetry is, however, unreliable in the presence of methemoglobinemia since methemoglobin (MetHb) absorbs light equally well at wavelengths (typically 660 nm and 940 nm) used to determine oxygen saturation. Arterial blood gas analysis can be also misleading in methemoglobinemia because it will show normal partial pressure of oxygen even in the presence of high MetHb concentration and inaccurate oxygen saturation if values were calculated from the pH and $P_aO_2$. Co-oximetry is generally the principal laboratory technique used for the diagnosis of methemoglobinemia. Unfortunately, because co-oximetry relies on the absorption spectra of a few wavelengths for the calculation of MetHb concentration, false positive readings often result from the presence of other pigments such as methylene blue or sulfhemoglobin which have high absorption at the methemoglobin absorption peak at around 630 nm. Moreover, with co-oximetry, intermittent blood drawing is necessary and it is important to use fresh specimens for analysis as methemoglobin levels rise with storage time.

During the therapeutic stage of methemoglobinemia, methemoglobin can be reduced back to hemoglobin either enzymatically or non-enzymatically via a number of pathways. For drug-induced methemoglobinemia, methylene blue (MB) is a standard treatment modality. However, being an oxidant itself, large doses of methylene blue will overwhelm the reducing effect of leukomethylene blue, and can result in hemolysis and, paradoxically, methemoglobinemia in patients with glucose phosphate dehydrogenase (G6PD) deficiency. Unfortunately, the three aforementioned existing diagnostic methods (pulse oximetry, arterial blood gas analysis, and co-oximetry) are incapable of simultaneously quantifying in vivo tissue concentrations of MetHb and MB as well as oxyhemoglobin ($Hb-O_2$) and deoxyhemoglobin (Hb-R) to monitor progression and resolution of methemoglobinemia.

There thus is a need for a method and device that can be used to dynamically monitor multiple in vivo tissue chromophores in a non-invasive manner. In addition, the method and device must have a sensitivity that is necessary from effective therapeutic monitoring. Preferably, there is a need for a method and device that permits real time or near real time concentration measurements of MetHb, Hb-R, $Hb-O_2$, $H_2O$, and MB. While a need exists for dynamically monitoring multiple chromophores to monitor progression and resolution of methemoglobinemia, it should be understood that needs also exist for additional diseased or abnormal states beyond methemoglobinemia. The device and method should be useful in evaluating the dynamics of drug delivery and therapeutic efficacy in blood chemistry. Preferably, the method and device can be used to dynamically monitor a variety of chromophores in vivo.

SUMMARY OF THE INVENTION

The present invention is directed to a method and device that uses broadband diffuse optical spectroscopy to dynamically calculate and monitor the concentrations of multiple chromophores in a sample of biological tissue (e.g., tissue of a subject) in a non-invasive manner. A method for monitoring the concentrations of multiple chromophores in a subject includes the step of providing a broadband diffuse optical spectroscopy device, the device having a first light source emitting light at a plurality of wavelengths and a second light source including a broadband light source. The first light source is optically coupled to a first source optical fiber that terminates in a probe. The second light source is optically coupled to a second source optical fiber that terminates in the probe. The device further includes a first detector optical fiber optically coupled to a detector and a second detector optical fiber optically coupled to a spectrometer, the first and second detector optical fibers also terminating in the probe.

The method includes the steps of radiating the subject with light from the first light source, detecting intensity-modulated diffuse reflectance signals using the detector, determining absorption and reduced scattering coefficients at each wavelength of the first light source, radiating the subject with radiation from the second light source, acquiring steady-state broadband reflectance measurements using the spectrometer, determining absolute reflectance spectra based on the steady-state broadband reflectance measurements and the absorption and reduced scattering coefficients, calculating $\mu_a$ spectra from the absolute reflectance spectra, and determining the concentration of the multiple chromophores based on wavelength-dependent extinction coefficient spectra of each chromophore.

In another aspect of the invention, a broadband diffuse optical spectroscopy device for monitoring the concentrations of multiple chromophores in vivo includes first and second light sources, the first light source emitting light at a plurality of wavelengths and the second light source including a broadband light source. A first source optical fiber is optically coupled to the first light source at a proximal end and terminates at the probe at the distal end. A second source optical fiber is optically coupled to the second light source at a proximal end and terminates at the probe at the distal end. The device includes a first detector optical fiber optically coupled to a detector at a proximal end and terminating at the probe at the other end. The device also includes a second detector optical fiber optically coupled to a spectrometer at a proximal end and terminating at the probe at the distal end. A computer interfaces with the detector and the spectrometer and calculates the concentrations of the multiple chromophores based on intensity-modulated diffuse reflectance signals detected at the detector and steady-state reflectance measurements made by the spectrometer.

In one aspect of the invention, the optical fibers terminate in a probe having a distal face that is oriented generally perpendicular to the long axis of the probe. In another aspect of the invention, the optical fibers terminate in a probe having a exit face that is oriented generally planar to the long axis of the probe. In this latter embodiment, the incoming and outgoing light is bent or turned through an angle of about 90°. The probe may be taped, clamped, wrapped, or adhered to the skin of a patient.

In yet another aspect of the invention, a method of monitoring methemoglobinemia in a subject includes the steps of providing a broadband DOS device as described herein. The subject is irradiated with light from the first light source. Intensity-modulated diffuse reflectance signals are detected using the detector. Absorption and reduced scattering coefficients are determined at each wavelength of the first light source. The subject is irradiated with light (e.g., radiation) from the second light source. Broadband reflectance measurements are acquired using the spectrometer. Absolute reflectance spectra is determined based on the broadband reflectance measurements and the absorption and reduced scattering coefficients. $\mu_a$ spectra is then calculated from the absolute reflectance spectra. The concentration of at least two chromophores are detected based on wavelength-dependent extinction coefficient spectra, the chromophores being selected from the group consisting of methemoglobin, deoxyhemoglobin, oxyhemoglobin, water, and methylene blue.

It is an object of the invention to provide a broadband diffuse optical spectroscopy device and method that can dynamically monitor multiple in vivo tissue chromophores in a non-invasive manner. It is a further object of the invention to provide a device and method to non-invasively dynamically monitor multiple in vivo tissue chromophores for therapeutic monitoring of a patient.

The present invention employs a quantitative method based on broadband diffuse optical spectroscopy (DOS) that combines multi-frequency frequency-domain photon migration (FDPM) methods with NIR spectroscopy. Broadband DOS can be used to dynamically monitor in vivo concentrations of multiple chromophores such as MetHb, MB, Hb-$O_2$, Hb-R, and water in tissue non-invasively. Particular emphasis is placed on DOS sensitivity to dynamic changes in chromophore concentrations and physiological information that can be used to assess the success or failure of therapeutic interventions.

Unlike arterial blood gas analysis, pulse oximetry, and co-oximetry, broadband DOS is able to non-invasively quantify real-time changes in MetHb and four additional tissue components (Hb-R, Hb-$O_2$, $H_2O$, and MB) with sub-micromolar sensitivity and significant overlapping spectral features.

The present device and method can be used to monitor therapeutic treatment of methemoglobinemia using methylene blue. Also, the device and method can be used for cyanide toxicity treatment with therapeutically induced methemoglobin and in neonatal methemoglobinema management during inhaled nitric oxide treatment for hypoxemic respiratory failure. In addition to specific examples described above, this technique is expected to be useful in evaluating dynamics of drug delivery and therapeutic efficacy in blood chemistry, human, and pre-clinical animal models.

BRIEF DESCRIPTION OF THE DRAWINGS

FIG. 5 is a graph illustrating the formation of MetHb over time with the administration of 0.1 cc amyl nitrite bolus into a subject. The graph also illustrates the oxidation of Hb-$O_2$ to MetHb. As seen in FIG. 5, the concentration of Hb-R increased less than 1%.

DETAILED DESCRIPTION OF THE PREFERRED EMBODIMENTS

Figure 1:
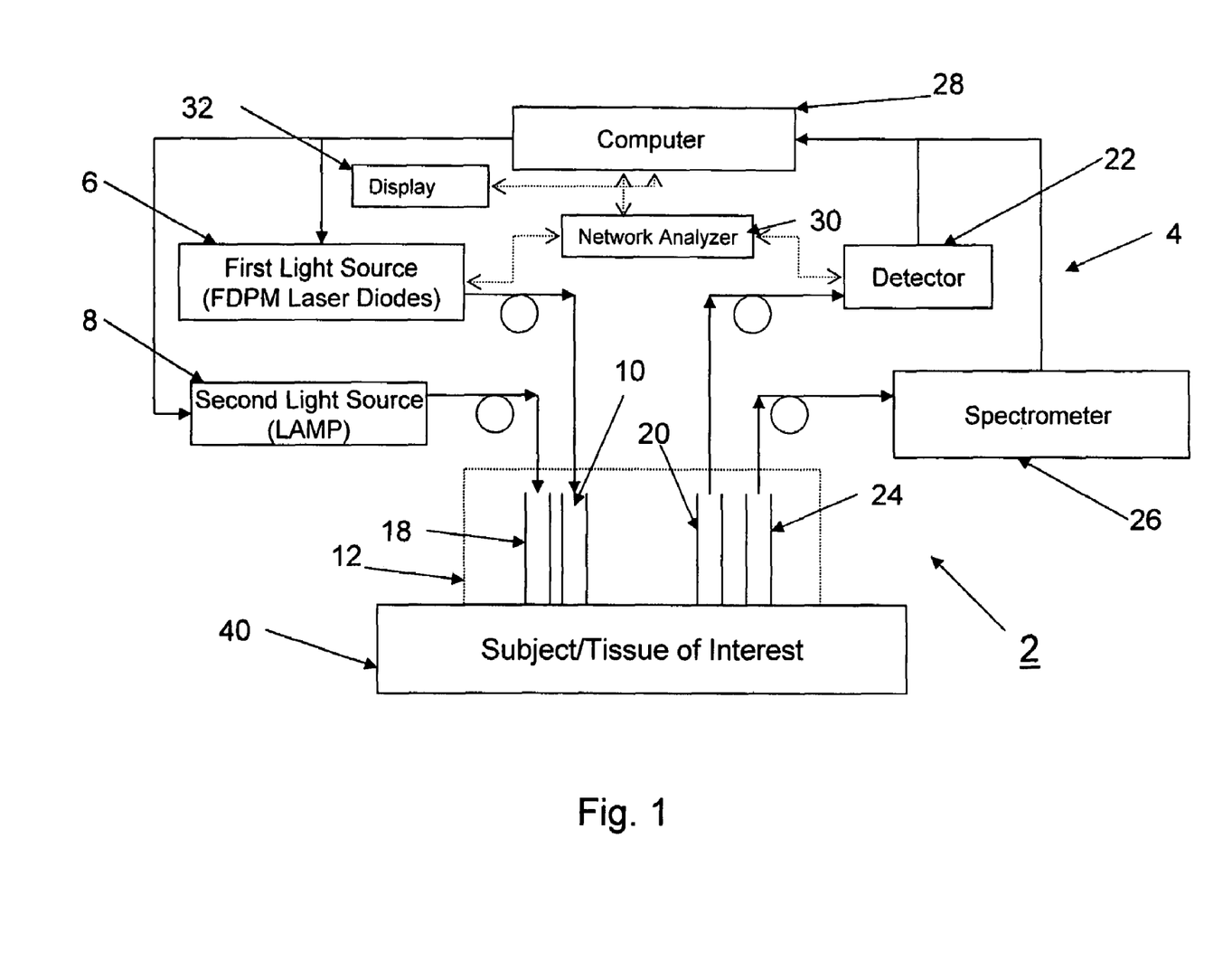
FIG. 1 illustrates a broadband diffuse optical spectroscopy (DOS) system according to one aspect of the invention.

FIG. 1 illustrates a system 2 according to a preferred aspect of the invention. The system 2 generally includes a diffuse optical spectroscopy (DOS) device 4. The DOS device 4 includes a first light source 6 which preferably emits radiation at multiple wavelengths. For example, the first light source 6 may comprise multiple laser diodes each operating a different wavelengths. One exemplary example uses six laser diodes operating at wavelengths of 661 nm, 681 nm, 783 nm, 823 nm, and 910 nm. Another exemplary example includes six laser diodes operating at wavelengths of 658 nm, 682 nm, 785 nm, 810 nm, 830 nm, and 850 nm. Generally, at least three wavelengths are used to obtain FDPM measurements. In addition, in one aspect of the invention, the wavelengths are chosen within the range of about 600 nm to about 1000 nm. The plurality of laser diodes may be successively switched using a computer-controlled diode controller (ILX Lightwave LDC-3916 Laser Diode Controller) coupled to a series of RF switches (Keithley Model 2750 Multimeter/Switch System) (not shown).

Figure 2A:
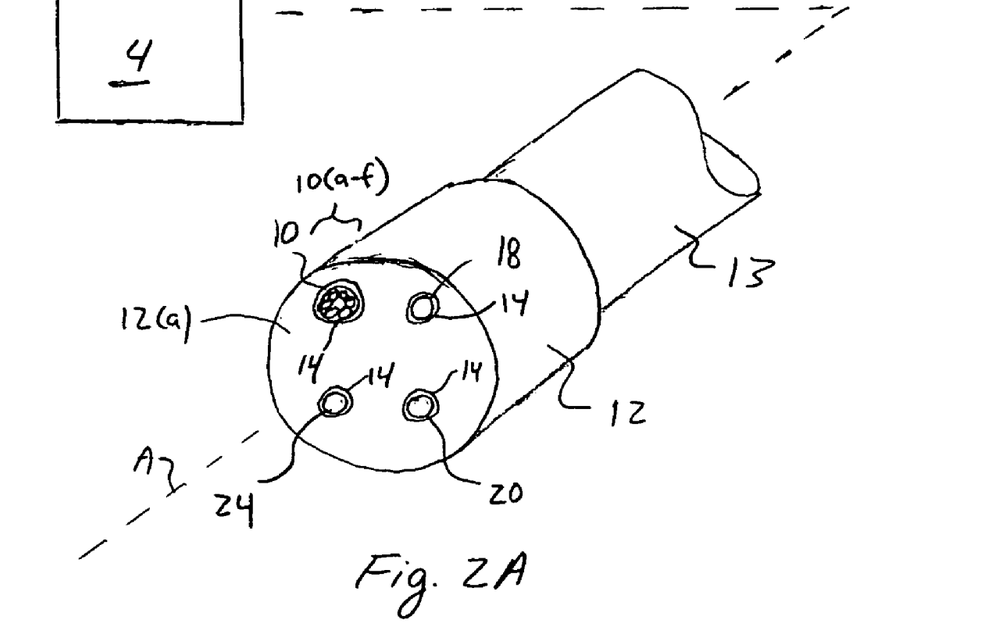
FIG. 2A illustrates a perspective view of a distal end of a probe used in connection with the DOS system shown in FIG. 1.
Figure 2B:
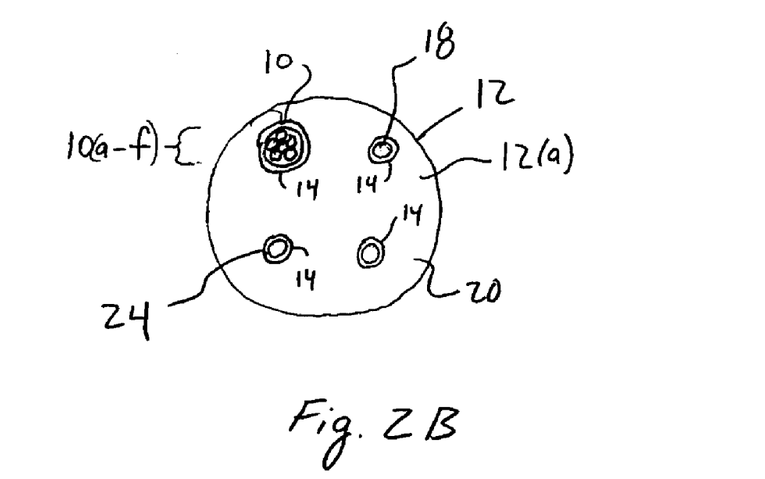
FIG. 2B illustrates an end view of the dital end of the probe shown in FIG. 2A.
Figure 3:
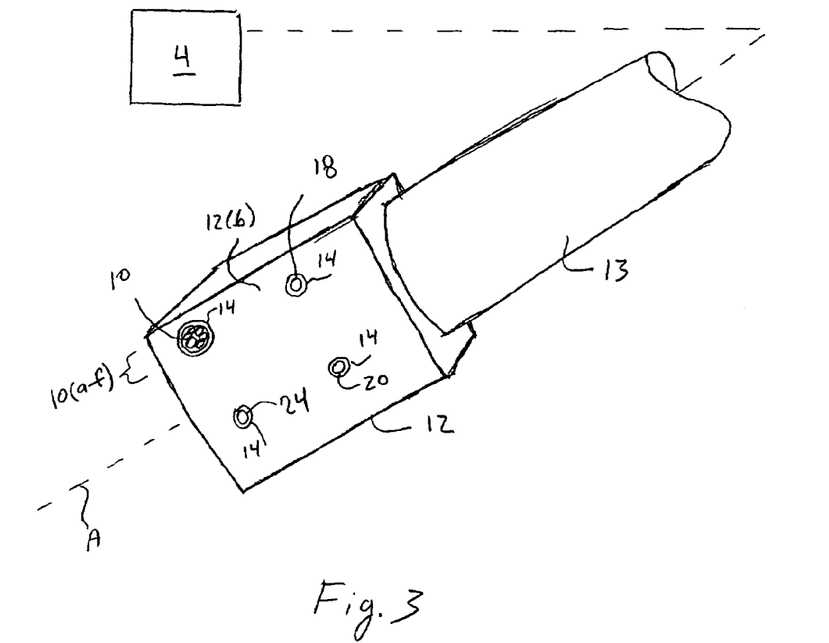
FIG. 3 illustrates an alternative embodiment of the probe according to one aspect of the invention.

The device 4 further includes a second light source 8 which generally serves as a broadband light source. The second light source 8 may comprise, for example, a tungsten-halogen light source (e.g., HL-2000-HP Ocean Optics). A first source optical fiber 10 is provided that is connected at one end (e.g., a proximal end) to the first light source 6 (FIG. 1 shows the distal-most portion of the optical fiber 10). The opposing or distal end of the first source optical fiber 10 preferably terminates in a probe 12 or other housing as is shown in FIGS. 2A, 2B and 3. The probe 12 may be formed from a plastic or resin-based material and include therein a plurality of holes or bores 14 (shown in FIGS. 2A and 2B) to receive optical fiber such as the source optical fiber 10. The first source optical fiber 10 is then secured inside the hole or bore 14 using an epoxy or other cementing material (not shown). The first source optical fiber 10 may include, for example, a plurality of 400 µm multimode optical fibers. In a preferred aspect of the invention, the first source optical fiber 10 may include a bundle of fibers formed from a plurality of individual fibers 10(a-f) (as is shown in FIGS. 2A, 2B, and 3) that are optically coupled to respective laser diodes. As best seen in FIG. 2A, the probe 12 is connected or otherwise affixed on a positioning member 13. The positioning member 13 may be flexible or inflexible depending on the particular use of the device 4. In one example, the positioning member 13 is an inflexible casing or tubing (e.g., stainless steel) that protects the optical fibers (10, 18, 20, 24) while the fibers are secured to the probe 12. In an alternative embodiment, a flexible positioning member 13 may be advantageous to facilitate the placement of the probe 12 against the skin of a subject 40. The positioning member 13 may include a tubular member, sheath, or wrap that retains or holds the optical fibers therein as they pass proximally from the probe 12 to the DOS device 4. The positioning member 13 preferably includes a lumen therein to hold the optical fibers (10, 18, 20, 24).

In one aspect of the invention, as is shown in FIGS. 2A and 2B, the distal face 12(a) of the probe 12 has a generally flat or planar surface which interfaces with or contacts a subject or tissue of interest 40 (e.g., a subject). The distal face 12(a) is generally oriented perpendicular to the long axis of the probe 12 (shown by dashed line A). The distal ends of the optical fibers (10, 18, 20, 24) may terminate in (e.g., are substantially flush with) the distal face 12(a). During monitoring of methemoglobinemia (or other condition) with the system 2, the distal face 12(a) of the probe 12 is placed against the skin or other surface of the subject 40. The probe 12 may be secured to the subject using an adhesive, tape, wrap, or the like to keep the distal face 12(a) against the surface of the subject's skin 40. In certain subjects, the skin may need to first be shaved to remove any hair that may interfere with the chromophore measurements.

FIG. 3 illustrates an alternative embodiment of the probe 12. As seen in FIG. 3, the probe 12 includes a face 12(b) that is oriented in a plane that is generally planar to the long axis (shown by dashed line A) of the probe 12 and holds the terminating ends of the first source optical fiber 10, the second source optical fiber 18, the first detector optical fiber 20, and the second detector optical fiber 24. In this orientation, the outgoing and incoming light is generally directed perpendicular to the long axis of the probe 12 and positioning member 13 (when straight). The advantage of this embodiment of the probe 12 is that the probe 12 can be readily fastened or secured to a subject 40. For example, the probe 12 and/or positioning member 13 may be taped, clamped, wrapped, or adhered to the skin of a patient. In this embodiment, the incoming and outgoing light is directed generally perpendicular to the long axis of the probe 12 and positioning member 13 by either bending the individual optical fibers or, alternatively, using one or more mirrored or refractive surfaces to manipulate the light through a generally 90° bend. For example, right-angle prisms may be disposed at the tips of the fibers (10, 18, 20, 24) to bend the light through approximately 90°. This side-firing arrangement allows for a more flexible placement of the probe 12.

In one aspect of the invention, as seen in FIG. 1, the device 4 includes a second source optical fiber 18 that is connected at one end (e.g. a proximal end) to a second light source 8 (FIG. 1 shows the distal-most portion of the optical fiber 18). The second source optical fiber 18 may include, for example, a 1000 µm multimode optical fiber. The opposing or distal end of the second source optical fiber 18 terminates in a probe 12 or other housing as is described above. The second source optical fiber 18 is then secured inside a hole or bore 14 in the probe 12 using an epoxy or other cementing material. In an alternative embodiment, a single or common source optical fiber (not shown) may be connected to the first and second light sources (6, 8), respectively.

Still referring to FIG. 1, the device 4 also includes a first detector optical fiber 20 that is coupled at one end (e.g., proximal end) to a detector 22 (FIG. 1 illustrates the distal portion of optical fiber 20). The detector 22 may include, for example, an avalanche photo diode (APD) detector (e.g., Hamamatsu high-speed APD module C5658). The opposing or distal end of the first detector optical fiber 20 terminates in a probe 12 or other housing. The opposing end of the first detector optical fiber 20 is then secured inside a hole or bore 14 in the probe 12 using an epoxy or other cementing material. Exemplary fibers that may be used as the first detector optical fiber 20 include a 1000 µm multimode optical fiber.

In one preferred aspect of the invention, the device 4 includes a second detector optical fiber 24 that is coupled at one end to a spectrometer 26. The spectrometer 26 preferably is able to acquire broadband reflectance measurements within the range of about 650 nm to about 1000 nm. One exemplary spectrometer 26 includes the Oriel MS 127i Intraspec IV CCD spectrometer available from Newport Corporation, Irvine, Calif. The opposing or distal end of the second detector optical fiber 24 terminates in a probe 12 or other housing. The opposing end of the second detector optical fiber 24 is then secured inside a hole or bore 14 in the probe 12 using an epoxy or other cementing material. The second detector fiber 24 may be formed, for example, with a 1000 µm multimode optical fiber.

FIG. 2B illustrates an end view of the probe 12 according to one aspect of the invention. As seen in FIG. 2B, the first source optical fiber 10 is shown as a bundle of optical fibers 10(a-f) disposed in a first quadrant of the probe 12 (upper left as shown in FIG. 2B). A second source optical fiber 18 is disposed in a second quadrant of the probe (upper right as shown in FIG. 2B). A first detector optical fiber 20 is located in a third quadrant of the probe 12 (lower right as shown in FIG. 2B). Generally, the first detector optical fiber 20 is diagonally opposed from the first source optical fiber 10. In one aspect of the invention, the first source optical fiber 10 is separated from the first detector optical fiber 20 by a distance of around 10 mm. A second detector optical fiber 24 is located in a fourth quadrant of the probe 12 (lower left as shown in FIG. 2B). The second detector optical fiber 24 is generally located diagonally opposite from the second source optical fiber 18. In one aspect of the invention, the second source optical fiber 18 is separated from the second detector optical fiber 24 by a distance of around 10 mm.

With reference to FIG. 1, the device 4 may include a computer 28 or central processor that is in electrical communication or otherwise interfaces with the first light source 6, the second light source 8, the detector 22, and spectrometer 26. The computer 28 may be a personal computer or the like having one or more data acquisition cards (not shown) for acquiring data from the detector 22 and spectrometer 26. Such data acquisition cards and the software for analyzing or manipulating the data are well known to those skilled in the art. In one aspect, the computer 28 may interface with or even include a network analyzer 30 such as the Hewlett Packard 8753E Network Analyzer that modulates the intensity and frequency of the first light source 6 (e.g., laser diodes).

The computer 28 and/or network analyzer 30 is preferably used to control the first light source 6 and the second light source 8. In addition, the computer 28 can be used to acquire data, calculate absorption and scattering coefficients, establish absolute reflectance intensities, calculate $\mu_a$, and calculate dynamic chromophore concentrations. Of course, the computer 28 may also include a display 32 or the like to display useful information to a user such as, for example, chromophore concentrations as a function of time on a real-time basis, time-elapsed graphs, and other parameters relevant to measuring chromophores. Moreover, the computer 28 may also be used to further manipulate the acquired data for subsequent analysis and/or display.

In accordance with one aspect of the invention, the subject or tissue of interest 40 is irradiated with light from the first light source 6. The intensity-modulated diffuse reflectance signals are then detected using the detector 22. Next, the absorption and reduced scattering coefficients are determined at each wavelength of the first light source using the computer 28. This is accomplished by fitting phase and amplitude data to the analytical diffusion solution as explained, for example, in F. Bevilacqua et al., "Broadband absorption spectroscopy in turbid media by combined frequency-domain and steady-state methods," Appl. Opt. 39,6498-6507 (2000), which is incorporated by references as if set forth fully herein.

Next, the subject or tissue of interest 40 is then irradiated with radiation from the second light source. Broadband reflectance measurements are then acquired using the spectrometer. The absolute reflectance spectra is then determined using the computer 28 based on the broadband reflectance measurements and the absorption and reduced scattering coefficients. Broadband absorption spectra ($\mu_a$) is then determined from the absolute reflectance spectra. Finally, the concentration of the multiple chromophores are determined based on wavelength-dependent extinction coefficient spectra of each chromophore. Typically, this last step may be performed by using a least-squares fit of the absorption spectra of the multiple chromophores to the measured absorption spectrum over a range of wavelengths (e.g., 650 nm to 1000 nm).

Figure 4:
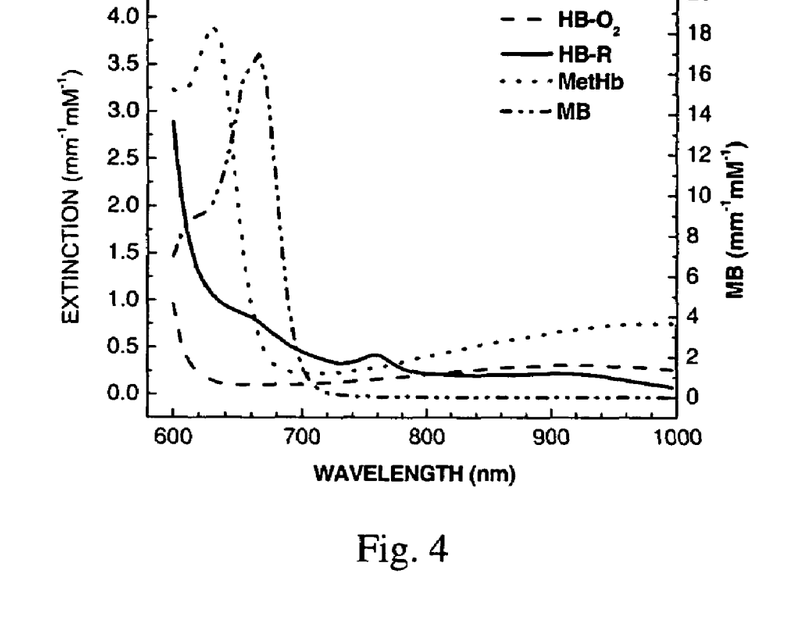
FIG. 4 illustrates the extinction coefficient spectra of hemoglobin species in near-infrared wavelengths between 600 nm and about 1000 nm.

With reference now to FIG. 4, the extinction coefficient spectra of hemoglobin species at near-infrared wavelengths between 600 nm and 1000 nm is illustrated. These species include methemoglobin (MetHb), deoxyhemoglobin (Hb-R), oxyhemoglobin (Hb-$O_2$), and methylene blue (MB). Methemoglobin (MetHb) is shown having an absorption peak around 630 nm.

In accordance with one aspect of the invention, the system 2 is used in a non-invasive manner to make quantitative in vivo measurements of methemoglobin formation and reduction in using broadband diffuse optical spectroscopy (DOS). Methemoglobinemia is an altered hemoglobin condition resulting from the oxidation of the ferrous moiety within the hemoglobin molecule. This conversion leads to abnormal oxygen affinity, reduced oxygen carrying capacity, and tissue hypoxia. Methemoglobinemia can be induced by multiple pharmacologic and chemical exposures including, for example, exposure to nitrites. For example, recreational usages of amyl nitrite, as well as nitrite contamination of water (e.g., well water) may induce methemoglobinemia. Significantly elevated levels of methemoglobin has also been observed reported in patients with sepsis, infants who develop severe metabolic acidosis (i.e., blue baby syndrome), as well as in individuals with rare congenital metabolic anomalies such as glucose-6-phosphate dehydrogenase (G6PD) deficiency. In addition, there have been reports wherein topical anesthesia such as lidocane and benzocaine may induce methemoglobinemia. Severe untreated methemoglobinemia can lead to delirium and death. Complaints by patients can be vague and typical diagnostic testing can often be misleading. Therapeutic implications can range anywhere from observation to admission into the intensive care unit for further management.

Because methemoglobinemia is a potentially life-threatening illness, early recognition of methemoglobinemia is crucial. Moreover, it is particularly important to monitor the effects of therapy such as, for example, the administration of methylene blue (MB). Traditional diagnostic modalities for subjects suffering from methemoglobinemia include pulse oximetry, arterial blood gas analysis, and co-oximetry. Pulse oximetry is, however, unreliable in the presence of methemoglobinemia since MetHb absorbs light equally well at wavelengths (typically 660 nm and 940 nm) used to determine oxygen saturation.

Arterial blood gas analysis may also be misleading in methemoglobinemia because the analysis will show normal partial pressure of oxygen even in the presence of high MetHb concentration. Moreover, blood gas analysis may produce inaccurate oxygen saturation if values were calculated from the pH and $P_aO_2$.

Co-oximetry is generally the current preferred laboratory technique for diagnosis of methemoglobinemia. However, co-oximetry, which relies on the absorption spectra of a few wavelengths for the calculation of MetHb concentration, may produce false positive readings resulting from the presence of other pigments such as methylene blue or sulfhemoglobin which have high absorption levels at the methemoglobin absorption peak at around 630 nm. In addition, co-oximetry is an invasive procedure, requiring intermittent blood drawing of fresh specimens for analysis since methemoglobin levels can rise with storage.

Once formed, methemoglobin can be reduced back to hemoglobin either enzymatically or non-enzymatically via a number of pathways. For drug-induced methemoglobinemia, methylene blue (MB) is a standard treatment modality because methylene blue serves as an exogenous electron acceptor and works as a cofactor for NADPH (reduced nicotinamide adenine nucleotide phosphate) reductase to reduce hemoglobin back to the original ferrous state. However, large doses of methylene blue can result in hemolysis and, paradoxically, methemoglobinemia in patients with glucose phosphate dehydrogenase (G6PD) deficiency.

Most chemical reactions involving the heme group cause detectable changes in hemoglobin's visible absorption spectrum. The oxidation of hemoglobin results in a marked increase of absorption in the red region of the visible spectrum (600 nm to 650 nm). As shown in FIG. 4, methemoglobin has a strong absorption peak at around 630 nm. This change of absorption spectra due to the formation and reduction of methemoglobin presents an optimal diagnostic platform for broadband diffuse optical spectroscopy (DOS). The system 2 and methods described herein combines multi-frequency frequency domain photon migration (FDPM) with time-independent near infrared (NIR) spectroscopy to quantitatively measure bulk tissue absorption and scattering spectra in wavelengths between the range of about 600 nm and about 1000 nm. As a result, the system 2 and method can rapidly quantify the in vivo concentrations of multiple tissue chromophores and exogenous dyes such as methylene blue non-invasively by use of the probe 12 that is placed adjacent to the skin or derma of a subject. Due to the quantitative description of tissue composition, the system 2 and method described herein can overcome the shortcomings of existing methemoglobinemia diagnostic modalities while providing additional valuable physiological information.

Experimental Results

The first objective of this experiment was to show that a stable in vivo animal model can be created with significant amounts of methemoglobin produced. The second objective was to show that the system 2 and method described herein which relies on broadband DOS can be used to detect and monitor the formation and resolution of methemoglobinemia. The experiments demonstrated that broadband DOS is capable of dynamic monitoring of multiple in vivo tissue chromophores non-invasively with sensitivities necessary for effective therapeutic monitoring.

In the experiment, tissue concentrations of methemoglobin [MetHb], deoxyhemoglobin [Hb-R], and oxyhemoglobin [Hb-$O_2$] were determined from absorption spectra acquired in "real-time" during nitrite infusions in five pathogen free New Zealand white rabbits. The system 2 was able to detect as little as 30 nM concentration changes in levels of MetHb that ranged from 1.42 to 4.2 µM, representing 2.2 to 10.6% of the total hemoglobin content (% MetHb). These values agreed well with ex vivo co-oximetry data from each rabbit (mean $r^2$=0.882±0.05, n=3). The reduction of MetHb to functional hemoglobins was also carried out with intravenous injections of methylene blue (MB). As little as 10 nM changes in MB concentration were detectable at levels of up to 150 nM in tissue. The results demonstrate the ability of the broadband DOS system 2 to non-invasively quantify real-time changes in MetHb and four additional tissue components (Hb-R, Hb-$O_2$, $H_2O$, and MB) with sub-micromolar sensitivity. The quantification of the concentration of the multiple chromophores is possible despite the fact that many of the components have significant overlapping spectral features.

In this experiment, a multi-wavelength, frequency domain instrument (FDPM) was combined with a steady state near infrared (NIR) spectrometer (see e.g., FIG. 1) and developed for the non-invasive in vivo assessment of MetHb formation and reduction. The device 4 employed six laser diodes (operating at 661 nm, 681 nm, 783 nm, 823 nm, 850 nm, and 910 nm) and a fiber-coupled avalanche photo diode (APD) detector (Hamamatsu high-speed APD module C5658). The APD detector detects the intensity-modulated diffuse reflectance signal at modulation frequencies between 50 to 550 MHz after propagating through the tissue. The absorption and reduced scattering coefficients are measured directly at each of the six laser diode wavelengths using the frequency-dependent phase and amplitude data. The reduced scattering coefficient is calculated throughout the NIR by fitting a power-law to these six reduced scattering coefficients. The steady-state acquisition is a broadband reflectance measurement from 600 nm to 1000 nm that follows the frequency domain (FD) measurements using a tungsten-halogen light source (FiberLite lamp) and a miniature spectrometer (Ocean Optics USB2000). The intensity of the steady-state (SS) reflectance measurements were calibrated to the FD values of absorption and scattering to establish the absolute reflectance intensity. The absolute steady-state reflectance spectra were then analyzed to calculate $\mu_a$ spectra. Finally, the tissue concentrations of the chromophores, i.e., Hb-$O_2$, Hb-R, MetHb, $H_2O$, and MB, were calculated by a linear least squares fit of the wavelength-dependent extinction coefficient spectra of each chromophore.

In the experiments, pathogen-free white New Zealand rabbits (Myrtle Rabbitry Inc., Thompson Station, Tenn.), weighing between ~3.5 to 4.1 kg, were used. Animals were housed in a pathogen-free animal facility and were given a commercial basal diet and water ad libitum. The animals were initially sedated by an intramuscular injection of the mixture of Ketamine HCl (100 mg/ml, Ketaject, Phoenix Pharmaceutical Inc., St. Joseph, Mich.) and Xylazine (20 mg/ml, Anased, Lloyd Laboratories, Shenandoah, Iowa) at a dose of 0.75 cc/kg. The animal's body weight and temperature were assessed after sedation. A 22 gauge catheter was then placed and secured into the animal's marginal ear vein for the subsequent intravenous anesthesia injection. The animals were then immediately intubated with a 3.0 cuffed endotracheal tube and placed on mechanical ventilation (dual phase control respirator, model 32A4BEPM-5R, Harvard Apparatus, Chicago, Ill.) with following settings: tidal volume, 50 cc, respiratory rate 25 bits/min, and 100% supplemental oxygen. Blunt dissection was performed to isolate the femoral artery on the left thigh slightly distal to the inguinal ligament and a 20 gauge catheter was secured within the femoral artery for the systemic blood pressure measurements and arterial sampling. Pressure measurements were obtained with a calibrated pressure transducer (TSD104A Transducer and MP100 WSW System, Biopac Systems, Inc., Santa Barbara, Calif., USA).

A plastic probe of the type described herein (i.e., probe 12) composed of source and detector fibers (10, 18, 20, and 24) was placed on the medial surface of the right hind thigh for the broadband DOS measurements. A separation of 10 mm for the source and detector fibers (10, 18, 20, and 24) was used for both FD and SS acquisitions. The reduced scattering coefficients were acquired from FD measurements at the discrete diode laser wavelengths and fit prior to NaNO$_2$ (or amyl nitrite) bolus injection. SS measurements were performed every 750 ms during the entire measurement sequence. During this time it was assumed that long-term changes in tissue that could affect scattering were minimal in comparison to nitrites and MB induced variations in Hb spectra.

After various levels of NaNO$_2$ doses were tried, the optimal NaNO$_2$ (500 mg/60 ml normal saline) dosage was determined experimentally and administrated at a rate of 2.6 ml/min to allow for blood draws and titration of fluids and vasopressors for hemodynamic support. Arterial blood samples were obtained every 5-10 minutes until the blood obtained appeared visibly darker. MB boluses (15 mg/60 ml NS) were then infused five times at a rate of 7.9 ml/min. MB administration was stopped at regular intervals for arterial sampling. Both MB and NaNO$_2$ were infused using an automated infuser. Norepinephrine (4 mg/500 ml NS) was titrated to maintain systolic blood pressure above 80 mm Hg. Animals that developed distress or survived the induction and reversal of methemoglobinemia were euthanized by standard procedures.

Indirect oxidation of hemoglobin involves a process of co-oxidation in which amyl nitrite or sodium nitrite is co-oxidized with heme iron by Hb-O$_2$. The mechanism of nitrite-induced oxidation has been studied extensively because nitrites are an important cause of toxic methemoglobinemia. The oxidation of hemoglobin is recognized as an autocatalytic process by nitrites. Because nitrite is a univalent reductant of oxygen, the overall pathway generally involves the reduction of oxygen to superoxide (O$_2^-$) and hydrogen peroxide (H$_2$O$_2$). The reaction can be summarized as follows.

$$4HbFe^{2+}O_2 + 4NO_2^- + 4H^+ \rightarrow 4HbFe^{3+} + 4NO_3^- + 2H_2O + O_2 \quad (1)$$

For cases of methemoglobinemia resulting from drug exposure, MB is infused as the treatment. The activity of MB depends on the availability of reduced nicotinamide adenine nucleotide phosphate (NADPH) within the red blood cell. NADPH reductase reduces MB to leukomethylene blue (LMB), which acts as an electron donor, and MetHb is reduced back to hemoglobin.

$$MB + NADPH \rightarrow LMB + NADP^+ \quad (2)$$

$$LMB + HbFe^{3+} \rightarrow HbFe^{2+} + MB \quad (3)$$

Figure 5:
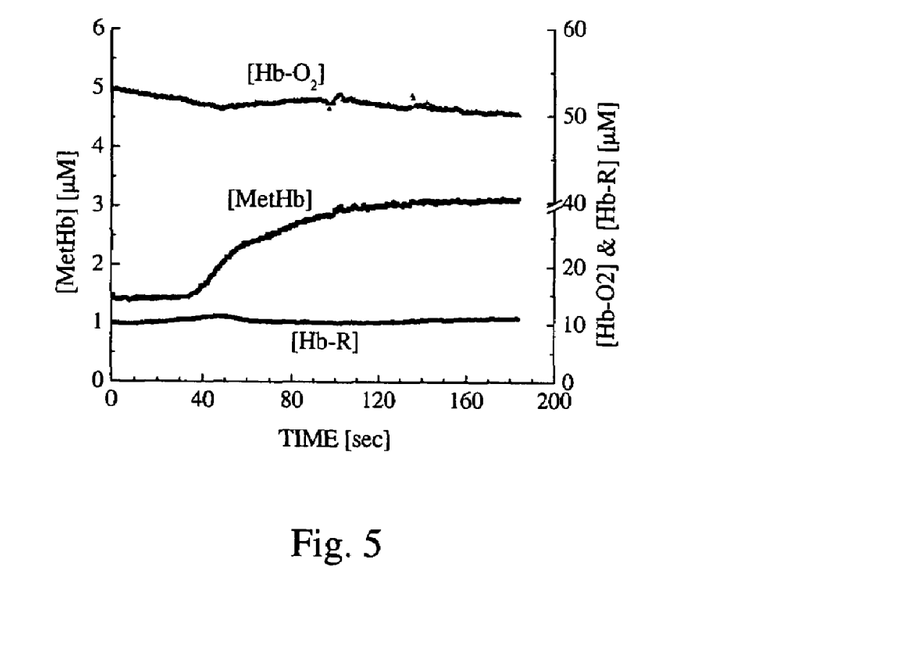

MetHb was successfully induced with a 0.1 cc amyl nitrite (AN) bolus. FIG. 5 shows the concentration changes of Hb-O$_2$, Hb-R, and MetHb after amyl nitrite injection. While the maximum concentration increase of Hb-R was less than 1%, the concentration of MetHb increased from 1.42 μM to 3.17 μM, representing 2.2% and 4.85% of the total hemoglobin concentration, respectively. In addition, there was a concurrent decrease in the concentration of Hb-O$_2$(~1.75 μM) during MetHb formation. The mean concentration of MetHb prior to AN injection was 1.42±0.02 μM, which represents the minimum detection limit of broadband DOS in the presence of endogenous MetHb. The sensitivity of measurement was established by fitting the concentration plot with Boltzmann function (r$^2$=0.995) and calculating the standard deviation of measurements from the fitting function (SD=29.4 nM). As a result, it was determined that broadband DOS system 2 was able to detect as little as 30 nM changes in the concentration of MetHb in tissue.

Figure 6:
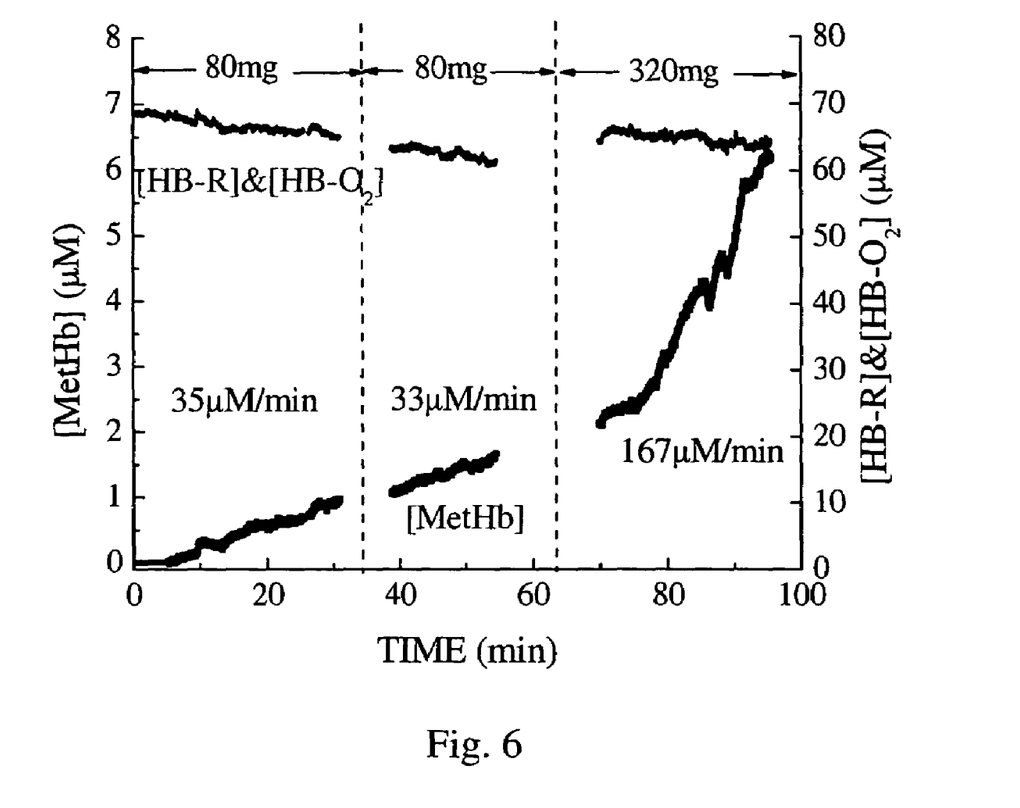
FIG. 6 is a graph illustrating the induction of methemoglobin with varying concentrations of sodium nitrite.

FIG. 6 illustrates the induction of MetHb utilizing two different concentrations of sodium nitrite (NaNO$_2$) solution. During the initial part of the study, 80 mg (in 60 cc NS) was administrated twice intravenously over the same time duration. The broadband DOS system 2 detected ferric oxidation at a rate of 35 μM/min and 33 μM/min, respectively. Quadrupling the dose (320 mg/60 cc NS) while administering NaNO$_2$ over similar time duration resulted in a corresponding formation rate increase at 167 μM/min. To maintain mean arterial blood pressure against the relaxation of small vessels by NaNO$_2$, LEVOPHED (noreopinephrine bitartrate) was titrated between 4 to 16 μg/min to keep blood pressure above 80 mmHg. The percentage of MetHb ([MetHb]/([Hb-O$_2$]+[Hb-R]+[MetHb])) from co-oximetry after 480 mg of NaNO$_2$ was 41.8% while the percentage of MetHb from the broadband DOS reached 8.8%. This large discrepancy was likely a result of continued oxidation of arterial blood due to the storage of the blood sample prior to co-oximetry analysis. This observation was confirmed in which a 2.74 fold (174%) increase was observed in absorbance at 630 nm after 45 minutes during standard in vitro spectroscopic measurements.

Figure 7A:
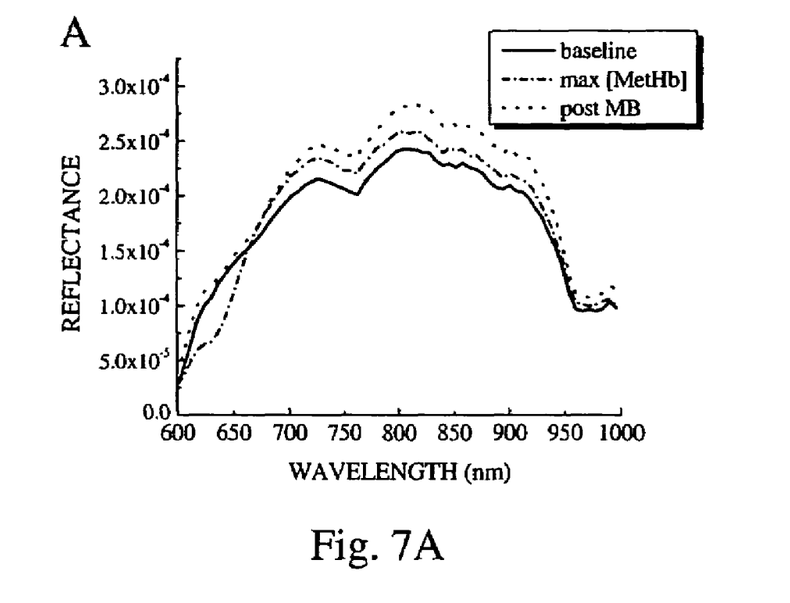
FIG. 7A is a graph illustrating the calibrated reflectance vs. wavelength of a subject undergoing methylene blue treatment. The solid line represents spectra at the baseline, the dash dotted line illustrates the maximum MetHb concentration, and dotted line illustrates the concentration at the end of (i.e., post) methylene blue treatment.
Figure 7B:
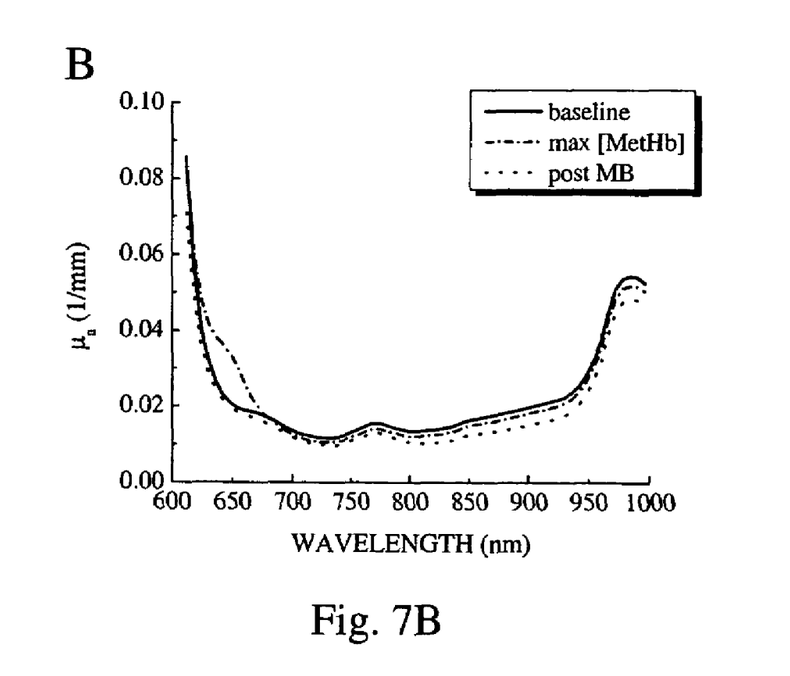
FIG. 7B is a graph illustrating the absorption vs. wavelength of the subject undergoing methylene blue treatment. The solid line represents spectra at the baseline, the dash dotted line illustrates the maximum MetHb concentration, and dotted line illustrates the concentration at the end of (i.e., post) methylene blue treatment.

After establishing a stable MetHb induction model using NaNO$_2$, the reduction of MetHb was attempted with 15 mg of MB (60 cc NS) following the intravenous administration of 500 mg NaNO$_2$ (60 cc NS) in three rabbits. Changes in the absolute reflectance and absorption coefficient, μ$_a$, at the baseline (solid line), at the maximum MetHb concentration (dash-dotted line), and post-MB treatment (dotted line) are shown in FIGS. 7A & 7B. Significant spectral changes in both reflectance (FIG. 7A) and μ$_a$ (FIG. B) occurred at the MetHb absorption peak of 630 nm. Reflectance values at the peak MetHb concentration decreased 37.3% from baseline and returned within 10% of baseline after MB treatment. Likewise, the absorption coefficient at 630 nm increased 58.1% from baseline at the peak MetHb concentration, returning to within 7% of baseline post MB treatment.

Figure 8A:
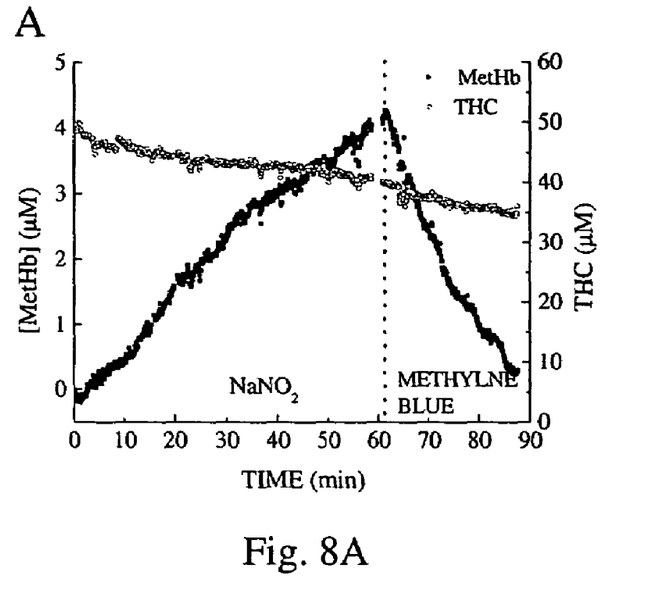
FIG. 8A illustrates a time course progression of THC (total hemoglobin concentration) and MetHb concentration during NaNO$_2$ and MB intervention for a subject.
Figure 8B:
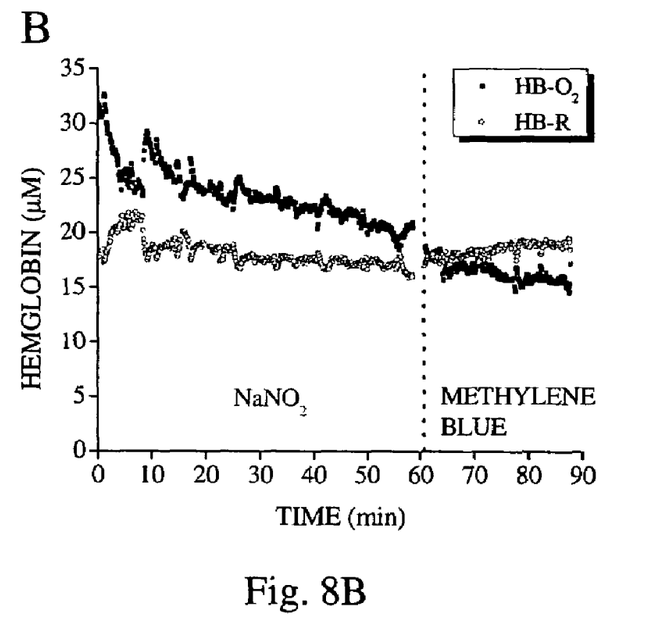
FIG. 8B illustrates a time course progression of Hb-$O_2$ and Hb-R concentration during NaNO$_2$ and MB intervention for a subject.

FIGS. 8A and 8B illustrate the in vivo time course concentration changes in MetHb, Hb-R, and Hb-O$_2$ measured by the broadband DOS system 2. FIG. 8A illustrates the increase in MetHb concentration during NaNO$_2$ administration and the subsequent decrease during MB treatment. These changes are consistent with the changes in absolute reflectance and μ$_a$ shown in FIGS. 7A and 7B. Total hemoglobin concentration (THC, which is the sum of Hb-R, Hb-O$_2$, MetHb) is also shown in FIG. 8A. In FIG. 8B, the concentration of Hb-O$_2$ decreased once the NaNO$_2$ injection started as the conversion from Hb-O$_2$ to MetHb took place.

Unlike the induction with amyl nitrite in FIG. 5, the decreasing trend in the THC was much more noticeable with NaNO$_2$ injections. Hemodilution from fluid resuscitation and large NaNO$_2$ diluent volume is the most likely origin of this decrease in THC. Using the hemoglobin concentration data (g/dL) obtained from co-oximetry, estimated initial blood volume (~50 cc/kg), and the amount of saline infused, it was estimated that THC would decrease approximately by 15.16%, 9.33%, and 12.50%, respectively for rabbit 1, 2, and 3.

Table 1, reproduced below, summarizes the comparable decreases in THC (sum of Hb-R, Hb-O$_2$ and MetHb concentration) at 15.65%, 11.49%, and 8.68% from broadband DOS measurements, respectively. The concentrations of Hb-R, Hb-O$_2$, and MetHb were measured by broadband DOS. BASE indicates the baseline measurement prior to NaNO$_2$ injection. MAX denotes the measurement point where MetHb concentration is the highest. END reflects the post-methylene blue treatment. The dosages of both NaNO$_2$ and MB are the total amounts injected to the particular rabbits.

TABLE 1

|  | WEIGHT (kg) | NaNO$_2$ (mg) | MB (mg) |  | Hb-R (μM) | Hb-O$_2$ (μM) | MetHb (μM) |
|---|---|---|---|---|---|---|---|
| Rabbit 1 | 4.1 | 300 | 15 | BASE | 27.45 | 19.85 | −0.12 |
|  |  |  |  | MAX | 18.04 | 17.65 | 4.22 |
|  |  |  |  | END | 15.60 | 19.06 | 0.30 |
| Rabbit 2 | 3.5 | 150 | 12.5 | BASE | 35.36 | 18.99 | −0.32 |
|  |  |  |  | MAX | 26.40 | 17.67 | 4.03 |
|  |  |  |  | END | 17.88 | 19.88 | −0.05 |
| Rabbit 3 | 4.2 | 250 | 15 | BASE | 31.27 | 22.04 | −0.09 |
|  |  |  |  | MAX | 26.22 | 18.09 | 4.38 |
|  |  |  |  | END | 18.96 | 22.00 | −0.01 |

Figure 9:
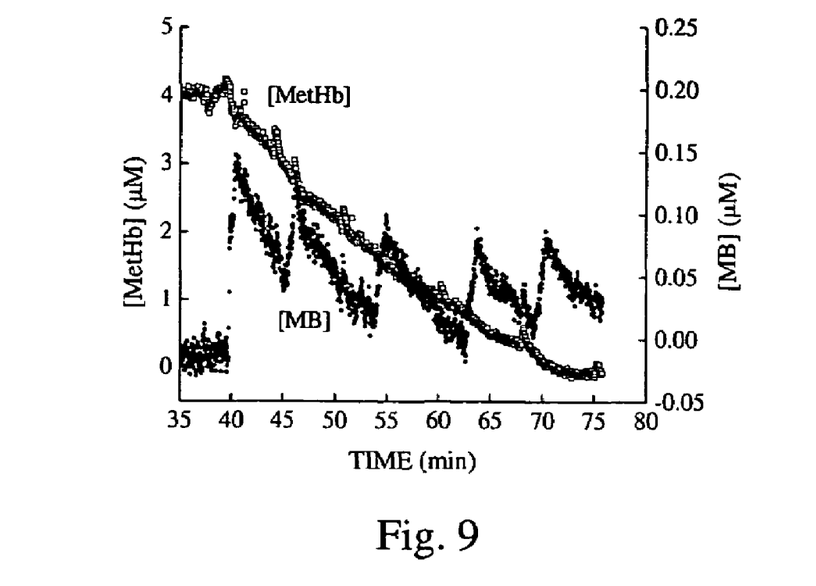
FIG. 9 is a graph illustrating the time-course concentration plots of MetHb and MB during reduction phase after the administration of a MB bolus.

FIG. 9 shows the time-course change of MB concentration during the reduction of MetHb. The concentration plot shows the five discrete injection points of MB and the extravasation. MB uptake and extravasation rates were extracted by linearly fitting each segment after MB bolus injections. Also, to estimate the utilization of each MB injection and kinetic rates of [MetHb] reduction, [MetHb] plots during five MB extravasation segments were fitted to a first order exponential decay. Calculated time constants, τ, for MetHb decay and rates of MB uptake and extravasation are summarized below in Table 2. The uptake and extravasation rates of MB was calculated by linearly fitting MB concentration plots. Decay time constants, t of MetHb were obtained with a single exponential decay fitting.

TABLE 2

| MB injection | MB Uptake [nM/min] | MB extravasation [nM/min] | MetHb Decay, τ [min] |
|---|---|---|---|
| 1 | 210 | −17 | 20.6 |
| 2 | 96 | −11 | 17.5 |
| 3 | 68 | −11 | 13.7 |
| 4 | 64 | −7 | 8.3 |
| 5 | 71 | −9 | N/A |

As seen in Table 2, uptake rates of MB decreased from 210 nM/min to 64 nM/min following four injections and extravasation rates of MB also followed the same trend. The MetHb decay time constants of five segments also decreased from 20.6 min. to 8.3 min., suggesting that MetHb reduction rates are related to available MetHb.

Figure 10:
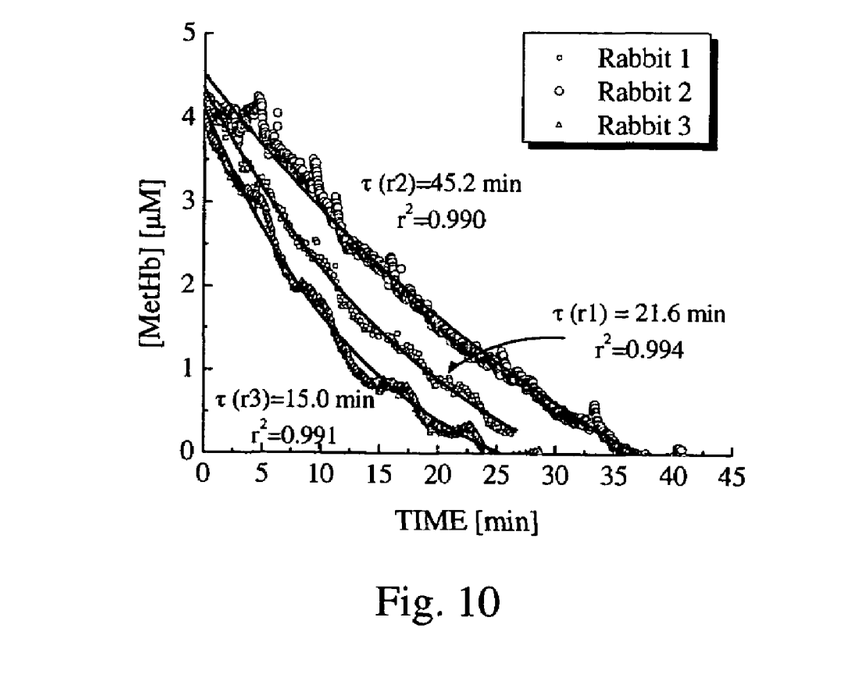
FIG. 10 illustrates the time constant comparison of three subject rabbits when [MetHb] plots were fitted with single exponential decay. Rabbit Nos. 1 and 3 were of similar weight (4.1 kg and 4.2 kg) and given a similar dosage of NaNO$_2$ and methylene blue. Rabbit No. 2 weighed less (3.5 kg) and was given a lower dosage of NaNO$_2$ (150 mg) and MB (12.5 mg).
Figure 11:
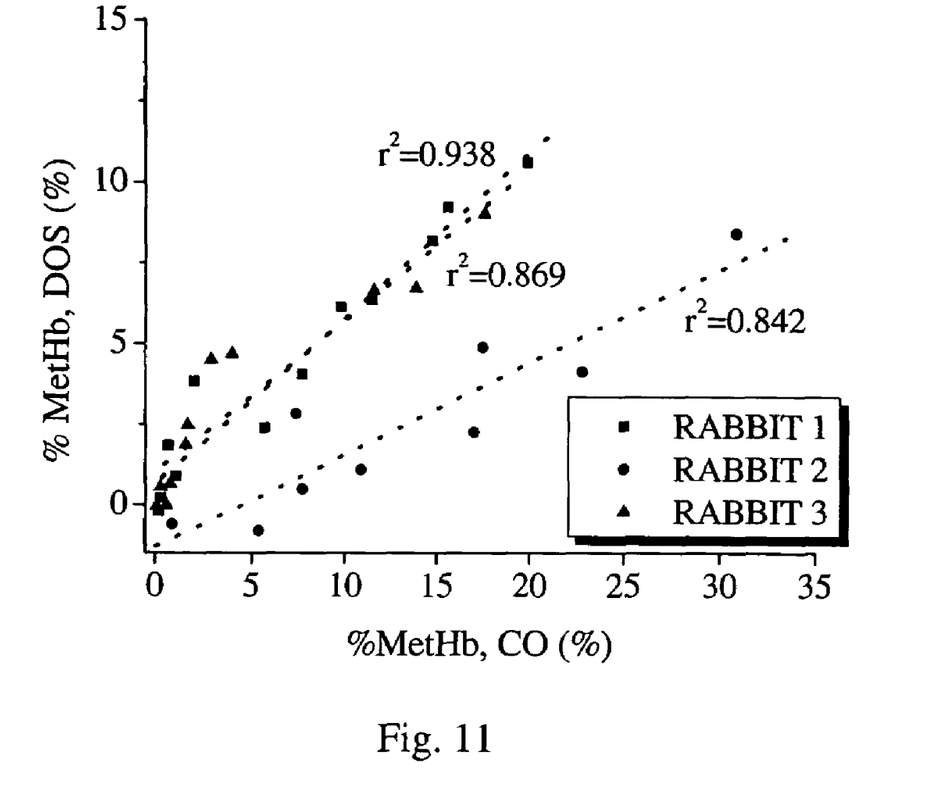
FIG. 11 shows the comparison of % MetHb between broadband DOS and co-oximetry $r^2$ values for three subjects (rabbits).

Overall MetHb decay kinetics of three rabbits were also calculated by fitting the broadband DOS decay plots in FIG. 10 employing a first order exponential decay function. Respective time constants, τ and correlation coefficients, $r^2$ are noted in FIG. 10. The intra-subject variation in physiological response ranged from τ=15.0 and 21.6 minutes (rabbits 1 and 3) to τ=45.2 minutes in rabbit 2. These time constants appeared to be related to MB dose and rabbit size.

The data acquired using the DOS system 2 was compared to the results obtained using co-oximetry, which is currently considered the benchmark or "gold standard" in monitoring methemoglobinemia. FIG. 10 shows a very close correlation in all three rabbit measurements between broadband DOS and co-oximetry values (mean $R^2$=0.882±0.05). As discussed previously, prolonged storage with an oxidizing agent before co-oximetry accounts for some of the discrepancies noted between broadband DOS measurements and those obtained by co-oximetry. Table 3, which is reproduced below, lists peak % MetHb from broadband DOS and co-oximetry of three animals and correlation coefficients between two measurement modalities.

TABLE 3

|  |  | RABBIT 1 | RABBIT 2 | RABBIT 3 |
|---|---|---|---|---|
| % MetHb (%) | CO-OXIMETER | 19.9 | 30.9 | 17.6 |
|  | DOS | 10.57 | 8.38 | 9.00 |
|  | CO-OX/DOS | 1.88 | 3.69 | 1.96 |

The DOS system 2 and methods described herein demonstrate that broadband DOS can be used to dynamically monitor in vivo concentrations of multiple chromophores in tissue in a non-invasive manner. The DOS system 2 and method is particularly sensitivity to dynamic changes in chromophore concentrations. The concentrations of multiple chromophores may be monitored and evaluated to assess the success or failure of therapeutic interventions.

The DOS system 2 and methods described herein may be used as a platform for investigating in vivo drug utilization kinetics. For example, the DOS system 2 and methods may be particularly useful in evaluating the dynamics of drug delivery and therapeutic efficacy. For example, the approach could be used in a clinical setting to gain insight on therapeutic efficacy, particularly in the cases of cyanide toxicity treatment with therapeutically induced MetHb and in neonatal methemoglobinema management during inhaled nitric oxide treatment for hypoxemic respiratory failure. Moreover, the DOS system 2 and method described herein may be used quantify and monitor the concentration of other chromophores such as, for example, lipids.

While embodiments of the present invention have been shown and described, various modifications may be made without departing from the scope of the present invention. The invention, therefore, should not be limited, except to the following claims, and their equivalents.

We claim:

1. A method of monitoring methemoglobinemia in a subject comprising the steps of:
   providing a broadband diffuse optical spectroscopy device, the device having a first light source emitting light at a plurality of wavelengths and second light source comprising a broadband light source, first and second source optical fibers optically coupled, respectively, to the first and second light sources, first and second detector optical fibers optically coupled, respectively, to a detector and a spectrometer, the broadband diffuse optical spectroscopy device including a probe that is configured for placement adjacent to the subject's skin;
   radiating the subject with light from the first light source;
   detecting intensity-modulated diffuse reflectance signals using the detector;
   determining absorption and reduced scattering coefficients at each wavelength of the first light source;
   radiating the subject with radiation from the second light source;
   acquiring broadband reflectance measurements using the spectrometer;
   determining absolute reflectance spectra based on the broadband reflectance measurements and the absorption and reduced scattering coefficients;
   calculating $\mu_a$ spectra from the absolute reflectance spectra; and determining the concentration of methemoglobin, deoxyhemoglobin, and oxyhemoglobin, based on wavelength-dependent extinction coefficient spectra;

calculating a percentage of methemoglobin based on the formula [MetHb]/([Hb-$O_2$]+[Hb-R]+[MetHb]); and displaying the percentage of methemoglobin on a computer display connected to the broadband diffuse optical spectroscopy device.

2. The method of claim 1, wherein at least one of the percentage and concentration methemoglobin is displayed on a display in real time.

3. The method of claim 1, wherein the broadband diffuse optical spectroscopy device is sensitive to 30 nM changes in MetHb levels.

4. The method of claim 1, further comprising the step of administering methylene blue to the subject and determining the concentration of methylene blue based on wavelength-dependent extinction coefficient spectra obtained from the broadband diffuse optical spectroscopy device and wherein the broadband diffuse optical spectroscopy device is sensitive to 10 nM changes in methylene blue levels.

5. The method of claim 4, further comprising displaying the concentration of deoxyhemoglobin, oxyhemoglobin, and methylene blue on the display.

6. A method of monitoring methemoglobinemia in a subject comprising the steps of:

providing a broadband diffuse optical spectroscopy device, the device having a first light source emitting light at a plurality of wavelengths and second light source comprising a broadband light source, a detector, and a spectrometer, the broadband diffuse optical spectroscopy device including a probe that is configured for placement adjacent to the subject's skin;

radiating the subject with light from the first and second light sources;

determining the concentration of methemoglobin, deoxyhemoglobin, and oxyhemoglobin based on wavelength-dependent extinction coefficient spectra obtained from the broadband diffuse optical spectroscopy device;

calculating a percentage of methemoglobin based on the formula [MetHb]/([Hb-$O_2$]+[Hb-R]+[MetHb]); and displaying at least one of the concentration and percentage of methemoglobin on a computer display operatively coupled to the broadband diffuse optical spectroscopy device.

7. The method of claim 6, further comprising the step of administering methylene blue to the subject and determining the concentration of methylene blue based on wavelength-dependent extinction coefficient spectra obtained from the broadband diffuse optical spectroscopy device.

8. The method of claim 6, wherein the at least one of concentration and percentage of methemoglobin is displayed on the display in real time.

9. The method of claim 6, wherein the broadband diffuse optical spectroscopy device is sensitive to 30 nM changes in MetHb levels.

10. The method of claim 7, wherein the broadband diffuse optical spectroscopy device is sensitive to 10 nM changes in methylene blue levels.

11. The method of claim 7, wherein the concentration of deoxyhemoglobin, oxyhemoglobin, and methylene blue are displayed on the display in real time.

12. A method of treating methemoglobinemia in a subject comprising the steps of:

providing a broadband diffuse optical spectroscopy device, the device having a first light source emitting light at a plurality of wavelengths and second light source comprising a broadband light source, a detector, and a spectrometer, the broadband diffuses optical spectroscopy device including a probe that is configured for placement adjacent to the subject's skin;

administering methylene blue to the subject;

radiating the subject with light from the first and second light sources;

determining the concentration of methemoglobin, deoxyhemoglobin, oxyhemoglobin and methylene blue based on wavelength-dependent extinction coefficient spectra obtained from the broadband diffuse optical spectroscopy device;

calculating a percentage of methemoglobin based on the formula [MetHb]/([Hb-$O_2$]+[Hb-R]+[MetHb]); and adjusting the administration of methylene based at least in part on the calculated percentage of methemoglobin.

13. The method of claim 12, wherein the percentage of methemoglobin is displayed on a display.

14. The method of claim 13, wherein the concentration of the methemoglobin is displayed on the display in real time.

15. The method of claim 12, wherein the broadband diffuse optical spectroscopy device is sensitive to 30 nM changes in MetHb levels.

16. The method of claim 12, wherein the broadband diffuse optical spectroscopy device is sensitive to 10 nM changes in methylene blue levels.

17. The method of claim 13, further comprising displaying the concentration of deoxyhemoglobin, oxyhemoglobin, and methylene blue on the display.

* * * * *